United States Patent [19]

Barri et al.

[11] Patent Number: 4,982,047
[45] Date of Patent: Jan. 1, 1991

[54] CHEMICAL PROCESS AND CATALYST

[75] Inventors: Sami A. I. Barri, South Ascot; Rabaab Tahir, Hounslow, both of England

[73] Assignee: The British Petroleum Company, p.l.c., London, United Kingdom

[21] Appl. No.: 370,372

[22] Filed: Jun. 23, 1989

[30] Foreign Application Priority Data

Jul. 14, 1988 [GB] United Kingdom ............... 8816721

[51] Int. Cl.$^5$ ............................................. C07C 5/333
[52] U.S. Cl. ................................................... 585/660
[58] Field of Search .......................................... 585/660

[56] References Cited

U.S. PATENT DOCUMENTS 4,020,011 4/1977 Nishikawa ......................... 252/441
4,438,288 3/1984 Imai et al. ......................... 585/379
4,665,267 5/1987 Barri .................................. 585/660
4,795,732 1/1989 Barri .................................. 502/223

FOREIGN PATENT DOCUMENTS 0212850 3/1987 European Pat. Off. .
0220525 5/1987 European Pat. Off. .
1366334 9/1974 United Kingdom .
2162534 2/1986 United Kingdom .

Primary Examiner—Curtis R. Davis
Attorney, Agent, or Firm—C. S. Lynch; D. J. Untener; L. W. Evans

[57] ABSTRACT

A catalyst which is substantially free of alkali and alkaline earth metals and comprises an effective amount of a platinum group metal on a silicalite support; characterized in that the catalyst also comprises tin. There is also provided a process for the dehydrogenation of a $C_2$ to $C_{10}$ paraffin to yield an alkene product, which comprises contacting the paraffin under dehydrogenation conditions with a catalyst according to the invention.

9 Claims, No Drawings

CHEMICAL PROCESS AND CATALYST

The present invention relates to a process for catalytically dehydrogenating hydrocarbons, to a novel dehydrogenation catalyst and to a process for producing the dehydrogenation catalyst.

Dehydrogenation is an important commercial process because of the great demand for olefins for the manufacture of a wide variety of chemical products such as detergents, high octane gasolines, pharmaceuticals, plastics, synthetic rubbers and many other chemical products.

To be commercially successful a dehydrogenation catalyst must satisfy at least three requirements, namely high activity, high selectivity and good stability. Activity is a measure of the catalyst's ability to convert dehydrogenatable hydrocarbons into products at a specified severity level, the severity level being a measure of the reaction conditions, i.e. temperature, pressure, contact time etc, employed. Selectivity is a measure of the catalyst's ability to convert dehydrogenatable hydrocarbons into a desired product or products relative to the amount of hydrocarbon charged or converted. Stability is a measure of the rate of change with time of the activity and selectivity factors.

Heterogeneous catalysts comprising platinum group metals for the dehydrogenation of liquid or gaseous hydrocarbons have been previously described. Representative of the prior art relating to platinum group metal catalysts are U.S. Pat. Nos. 3,531,543; 3,745,112; 3,892,657; 3,909,451; 4,101,593; 4,210,769; 4,329,258; 4,363,721; 4,438,288 and British Patent No. 1,499,297. Generally, in addition to the platinum group metal, there is employed a porous support and an additional component specifically selected for the purpose of improving the activity and/or selectivity and/or stability of the catalyst The additional component is typically an alkali metal or an alkaline earth metal. A large number of porous supports are reported. These include (1) activated carbon, coke, or charcoal; (2) silica or silica gel, silicon carbide, clays and silicates; (3) ceramics, porcelain, crushed firebrick, bauxite; (4) refractory inorganic oxides such as alumina, titania, zirconia and the like; (5) crystalline zeolite silicates; (6) spinels; and (7) combinations of the foregoing. U.S. Pat. No. 4 438 288 describes a dehydrogenation process employing, as catalyst, a platinum group metal and an alkali or alkaline earth component, on a porous support material. Amongst the porous support materials disclosed is silicalite.

EP-A-212,850 discloses that dehydrogenation catalysts comprising a platinum group metal and substantially free of an alkali and alkaline earth metal supported on a silicalite can exhibit not only a high activity and selectivity but also improved stability as compared with prior art catalysts. We have now found that these catalysts can be improved still further by the incorporation of tin.

Accordingly, the present invention provides a catalyst which is substantially free of alkali and alkaline earth metals and comprises an effective amount of a platinum group metal on a silicalite support; characterised in that the catalyst also comprises tin. The invention further provides a process for the dehydrogenation of a $C_2$ to $C_{10}$ paraffin to yield an alkene product which process comprises contacting the paraffin under dehydrogenation conditions with a catalyst which is substantially free of alkali and alkaline earth metals and comprises an effective amount of a platinum group metal on a silicalite support; characterised in that the catalyst also comprises tin.

Throughout this Specification, the term substantially free does not exclude trace amounts of materials that occur as impurities in ordinary commercially available materials.

The paraffin is preferably a $C_3$ to $C_6$ paraffin. Examples of suitable paraffinic hydrocarbons include ethane, propane, n-butane, isobutane, n-pentane, isopentane, n-hexane, 2-methylpentane, 3-methylpentane, 2,2-dimethylbutane, n-heptane and the like. The term paraffin is intended to include substituted paraffins for example ethyl benzene which upon dehydrogenation yields styrene.

The amount of tin present in the catalyst may vary widely. Preferably the catalyst contains from 0.05 to 20%, preferably from 0.1 to 15% by weight of tin. The tin is preferably present, at least in part, in elemental form.

The platinum group metal may suitably be at least one of platinum, ruthenium, iridium, rhodium or palladium and is preferably platinum. The metal is preferably present, at least in part, in elemental form. The catalyst may suitably contain up to 10%, preferably up to 5%, even more preferably from 0.01 to 2% by weight of the platinum group metal.

Silicalite is one form of crystalline silica polymorph and the term silicalite has been designated by Union Carbide. Silicalite can exist in a number of different structural forms depending upon the route by which it is prepared. Thus, one form (silicalite I) is described in U.S. Pat. No. 4,061,724 which relates to a silica polymorph consisting of crystalline silica which after calcination in air at 600° C. for one hour has a characteristic X-ray powder diffraction pattern similar to that of ZSM-5. Another form (silicalite II) is described in a publication in *Nature*, 280, 664–665 (1979) by D. M. Bibby, N. B. Milestone and L. P. Aldridge. Structurally, silicalite II has the same relationship to ZSM-11 as silicalite I has to ZSM-5. It has been proposed that silicalite I, for example, merely represents an extreme end member of the ZSM-5 type of aluminosilicate zeolite. These materials are designated as having the MFI structure. Silicalites utilisable as catalyst components in the operation of the present invention may contain minor amounts of impurities, such as aluminium and/or gallium, within the framework thereof. EP-A-212,850 contains a number of X-ray powder diffraction patterns of silicalite samples.

It is an advantage of the catalyst as used in the process of the present invention that no additional alkali metal or alkaline earth metal components are necessary for the performance of the invention. The risk of side reactions, such as cracking, and oligomerisation as a result of the acidic nature of certain of the prior art co-metals is reduced without the need to incorporate alkali metals. Catalyst preparation is thereby simplified.

The catalyst may suitably be prepared by any of the known techniques for preparing catalysts. These include impregnation, precipitation or gelation. A suitable method, for example, comprises impregnating a silicalite with a soluble thermally decomposable compound of tin and with a soluble thermally decomposable compound of the platinum group metal. A mineral acid, for example nitric acid, may be added to the impregnation solution or solutions in order to facilitate better the dispersion of the metallic component. The tin and the platinum group metal may be introduced together by impregnation with a single solution, or separately. If they are introduced separately, a preferred process comprises impregnating with a tin-containing solution; calcining the resultant material; impregnating with a platinum group metal-containing solution; and re-calcining.

The catalyst composition may if desired be sulphided and/or halogenated in known manner. It is, however, a major advantage of the catalysts of the invention that sulphiding is not necessary, and preferably the catalyst is substantially free from sulphur.

At some stage after impregnation it will be necessary to decompose thermally decomposable tin and platinum group metal compounds and preferably to activate reductively the catalyst composition.

In another aspect, the present invention provides a process for the production of a catalyst according to the invention, which process comprises forming a hydrogel comprising water, a soluble source of a platinum group metal, a source of silica and an organic nitrogen-containing compound and thereafter crystallising the hydrogel at elevated temperature; the process also comprising incorporating a source of tin before or after crystallisation of the hydrogel.

Of the platinum group metals, platinum is preferred. The metal may suitably be added in the form of a salt or complex thereof. Platinum, for example, may suitably be added in the form of tetramine platinum dihydroxide or dihalide, for example dichloride.

If desired, a source of tin may be added during preparation of the hydrogel. A salt or complex of tin is preferred.

Suitable sources of silica include, for example, sodium silicate, silica hydrosol, silica gel, silica sol and silicic acid. A preferred source of silica is an aqueous colloidal dispersion of silica particles. A suitable commercially available source of silica is LUDOX (RTM) Colloidal Silica supplied by Du Pont.

The organic nitrogen-containing compound may suitably be an amine, for example diethylamine or 1,6-diaminohexane, an alkanolamine, for example diethanolamine, or a tetraalkyl ammonium compound, for example tetrapropylammonium hydroxide or tetrabutylammonium hydroxide.

In addition to water, the hydrogel may if desired contain an alcohol, for example methanol or ethanol.

The proportions in which the water, silica source and organic nitrogen-containing compound are present in the hydrogel are such as to form one of the structurally distinct forms of silicalite. These proportions are disclosed in the aforesaid U.S. Pat. No. 4,061,724 and the article in Nature, 280, 664-665 (1979), which are incorporated herein by reference. The amount of the platinum group metal source may suitably be such as to provide up to 10% by weight, preferably up to 5% by weight, even more preferably between 0.01 and 2% by weight of the platinum group metal in the final catalyst composition.

Crystallisation may suitably be effected at a temperature greater than 100° C., preferably in the range from 140° to 220° C. The pressure may suitably be autogenous, that is the pressure generated within a closed vessel at the temperature employed. The crystallisation period will depend upon a number of factors including the rate of stirring and the temperature. Typically, within the preferred temperature range the crystallisation period may suitably be from 1 to 4 days.

The catalyst may be recovered, suitably by filtration or centrifugation, and washed, suitably with water at a temperature in the range, for example, of from 15° to 95° C.

Finally, the catalyst composition is preferably activated, suitably by a thermal treatment, for the purpose of decomposing thermally decomposable compounds. The thermal treatment may suitably be effected in the presence of an inert gas, for example nitrogen, or air. Alternatively, or in addition, the catalyst may be reductively activated by heating in the presence of a reducing gas, for example hydrogen. It is possible to combine the thermal treatment and the reductive treatment into a single operation.

If a source of tin was not present during preparation of the hydrogel, the tin may be incorporated by impregnation before or after activation of the catalyst.

As regards the process of the invention, dehydrogenation conditions suitably comprise a temperature in the range from about 300° to 800° C. and a pressure in the range from 0.01 to 10 bar. Since the dehydrogenation of hydrocarbons is an endothermic reaction and conversion levels are limited by chemical equilibrium, it is desirable in order to achieve high conversion to operate at high temperatures and low hydrogen partial pressures. Under severe conditions it is difficult to maintain high activity and selectivity for long periods of time because undesirable side reactions such as aromatisation, cracking, isomerisation and coke formation increase. Reaction conditions within the aforesaid ranges should be chosen with regard to maximising activity, selectivity and stability.

A diluent may be employed in the process. Suitable diluents include hydrogen, steam, methane, ethane and carbon dioxide. Preferably however the process is carried out without a diluent. It is an advantage of the process of the invention that, in general, large volumes of hydrogen are not required in order to render the process effective.

The product from the process of the invention comprises dehydrogenated hydrocarbons, unconverted dehydrogenatable hydrocarbons and hydrogen. It is preferred to recover hydrogen from the product. The hydrogen so-obtained may be utilised elsewhere or recycled to the dehydrogenation process as diluent. Depending upon the use to which the dehydrogenated hydrocarbon is to be put, it may be separated from the unconverted dehydrogenatable hydrocarbon. The separated unconverted hydrocarbons may then be recycled to the process.

Water or a material decomposable to water under dehydrogenation conditions, for example an alcohol, aldehyde, ether or ketone, may be admixed with the dehydrogenatable hydrocarbon either continuously or intermittently if so desired.

The invention will now be further illustrated by reference to the following Examples.

In the Examples and Comparison Tests the terms used are defined as follows:-

| | |
|---|---|
| WHSV ($h^{-1}$) | Weight hourly space velocity which is the weight of feed fed per weight of catalyst per hour, |
| Feed Conversion (wt %) | 100 − weight % of feed in the hydrocarbon products, |
| Selectivity to isobutene (wt %) | Weight % of isobutene in the hydrocarbon products × 100 per unit Feed Conversion. |

EXAMPLE 1—SYNTHESIS OF SILICALITE 600 grams of an aqueous solution containing 20% by weight tetrapropylammonium hydroxide (TPAOH) was added with stirring to 2000 grams of Ludox AS40 (Trade Mark, ex Dupont) containing 40% by weight silica (ammonia stabilised). The resultant hydrogel had the molar composition of:

4.4 TPAOH:1.4 $NH_3$:100 $SiO_2$:700 $H_2O$

The hydrogel was heated at 175° C. for 72 hours in a pressure vessel under autogenous pressure. The vessel was then cooled and the product was filtered, washed with distilled water and dried at 100° C. The X-ray powder diffraction pattern showed that the product was silicalite-1 (MFI-type structure) as characterised in EP-A-0212850.

EXAMPLE 2—TREATMENT OF SILICALITE

The silicalite sample was calcined at 600° C. in air for 48 hours. It was then stirred in 20% by weight nitric acid (silicalite/solution=0.25 by weight) for 1 hour at room temperature, filtered, washed with distilled water, dried and calcined again at 600° C. for 16 hours.

EXAMPLE 3—PREPARATION OF 0.5 WT % PT/SILICALITE—CATALYST A 30 grams of the treated silicalite was mixed with 150 grams of an aqueous solution containing 0.27 gram of $Pt(NH_3)_4Cl_2.H_2O$. The mixture was then dried in a rotary evaporator under vacuum in a water bath at 100° C. The solid was then placed in an air oven at 100° C. for 10-15 minutes.

EXAMPLE 4—PREPARATION OF 0.5 WT % PT/SN/SILICALITE—CATALYST B

The treated silicalite (30 grams) was mixed with 150 grams of propan-2-ol containing 1.9 grams of $SnCl_2.2H_2O$. The mixture was dried in a rotary evaporator and calcined at 600° C. as above. The solid was then mixed with 150 grams of aqueous solution containing 0.27 gram of $Pt(NH_3)_4Cl_2.H_2O$ and the mixture was dried in a rotary evaporator as above.

EXAMPLE 5—CATALYST PREPARATION AND ACTIVATION

Catalysts A and B were activated as follows before testing. The catalysts as prepared in Examples 3 and 4 were pressed at 14 tonnes pressure to form tablets and crushed and sieved to form 8 to 16 mesh (BSS) granules. The granules (approx. 5 cm³) were packed into a tubular quartz reactor which was 450 mm in length and 15 mm internal diameter. The reactor had a coaxial thermocouple well of approx. 3 mm outer diameter and the catalyst granules were sandwiched between two regions (each of 35 cm³) of inert beads.

Air (approx. 600 cm³/min) was passed over the catalyst and the temperature was raisd to 400° C. at the rate of 1.5° C./min and kept at 400° C. for at least 16 hours. The catalyst was then flushed with nitrogen and hydrogen was passed at 600 cm³/min. The temperature was then raised to the operating temperature at 1.5° C./min and kept at that temperature for at least 2 hours.

EXAMPLE 6—CATALYST TESTING

The activated catalysts as described above were tested for the dehydrogenation of isobutane in a continuous flow reactor. The results obtained and conditions used are given in the following Table. It can be seen from the results that use of the catalyst according to the invention lead to much improved selectivity to the desired product.

TABLE

DEHYDROGENATION OF ISO-BUTANE
Feed: isobutane
Pressure: atmospheric

| Catalyst | Temperature °C. | WHSV $h^{-1}$ | Feed Conversion % wt | Selectivity to iso-butene % wt |
|---|---|---|---|---|
| A | 530 | 1 | 64.2 | 37.6 |
|   | 530 | 4 | 43.7 | 76.9 |
|   | 590 | 4 | 63.0 | 45.0 |
| B | 530 | 2 | 42.0 | 70.6 |
|   | 590 | 2 | 53.3 | 67.4 |
|   | 530 | 4 | 31.2 | 86.3 |

We claim:

1. A process for the dehydrogenation of a $C_2$ to $C_{10}$ paraffin to yield an alkene product, which comprises contacting the paraffin under dehydrogenation conditions with a catalyst which is substantially free of alkali and alkaline earth metals and comprises an effective amount of a platinum group metal on a silicalite support; characterised in that the catalyst also comprises tin.

2. A process as claimed in claim 1, in which the temperature is from 300° to 800° C.

3. A process as claimed in either claim 1 in which the feedstock is a $C_3$ to $C_6$ paraffin.

4. A process as claimed in claim 1 in which the catalyst has been activated by thermal treatment prior to contact with the paraffin.

5. A process as claimed in claim 1 wherein said catalyst contains 0.1 to 15% by weight of tin.

6. A process as claimed in claim 1 in which the platinum group metal is platinum.

7. A process as claimed in claim 6 wherein said catalyst contains from 0.01 to 2% by weight of platinum.

8. A process as claimed in claim 6 wherein said catalyst contains 0.1 to 15% by weight of tin.

9. A process as claimed in claim 8 wherein said catalyst contains from 0.01 to 2% by weight of the platinum.

* * * * *

UNITED STATES PATENT AND TRADEMARK OFFICE
CERTIFICATE OF CORRECTION

PATENT NO. : 4,982,047

DATED : January 1, 1991

INVENTOR(S) : Sami A. I. Barri

It is certified that error appears in the above-identified patent and that said Letters Patent is hereby corrected as shown below:

Column 6, line 44;

In claim 3, line 1, delete the word "either".

Signed and Sealed this

Twelfth Day of May, 1992

Attest:

DOUGLAS B. COMER

*Attesting Officer*      *Acting Commissioner of Patents and Trademarks*